US012740975B2

(12) United States Patent
Arabi et al.

(10) Patent No.: US 12,740,975 B2
(45) Date of Patent: Sep. 22, 2026

(54) COMPOUNDS FOR THE TREATMENT AND PREVENTION OF CANCER

(71) Applicant: United Arab Emirates University, Al Ain (AE)

(72) Inventors: Alya A. Arabi, Al Ain (AE); Samir Attoub, Al Ain (AE); Hamda M. Aleissaee, Al Ain (AE); Thuraya Almessabi, Al Ain (AE); Muzna Almansouri, Al Ain (AE); Kholoud Arafat, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 19/022,468

(22) Filed: Jan. 15, 2025

(65) Prior Publication Data

US 2026/0199315 A1 Jul. 16, 2026

(51) Int. Cl.
*A61K 31/4545* (2006.01)
*A61P 35/00* (2006.01)

(52) U.S. Cl.
CPC .......... *A61K 31/4545* (2013.01); *A61P 35/00* (2018.01)

(58) Field of Classification Search
CPC ............................ A61K 31/4545; A61P 35/00
See application file for complete search history.

(56) References Cited

U.S. PATENT DOCUMENTS

2016/0193211 A1 7/2016 Lavitrano et al.
2020/0289506 A1 9/2020 Boiko et al.
2022/0117964 A1 4/2022 Yang et al.

FOREIGN PATENT DOCUMENTS

WO WO-2015048662 A2 * 4/2015 .......... A61K 31/444
WO 2024037594 A1 2/2024
WO 2024039925 A1 2/2024
WO 2024130344 A1 6/2024

OTHER PUBLICATIONS

Thiel, K. Structure-aided drug design's next generation. Nat Biotechnol 22, 513-519 (2004). https://doi.org/10.1038/nbt0504-513 (Year: 2004).*
Baselga, Jose. "Targeting tyrosine kinases in cancer: the second wave." Science 312.5777 (2006): 1175-1178. (Year: 2006).*
Anderson, Amy C. "The Process of Structure-Based Drug Design." Chemistry & Biology 2003: 787-797 (Year: 2003).*

(Continued)

*Primary Examiner* — Renee Claytor
*Assistant Examiner* — Elena V Vishnyakova
(74) *Attorney, Agent, or Firm* — MH2 Technology Law Group, LLP

(57) ABSTRACT

The present disclosure provides a use of compound of Formulae (I) to (V) for treatment or prevention of cancer. More particularly, the present disclosure provides a method of treating or preventing cancer by administering a therapeutically effective amount of a compound of Formula (I), Formula (II), Formula (III), Formula (IV) or Formula (V) to a subject in need thereof. More particularly, the present disclosure provides a compound of Formula (I), Formula (II), Formula (III), Formula (IV) or Formula (V), or a composition thereof for treatment of breast cancer by inhibiting the growth and/or viability of breast cancer cells.

16 Claims, 8 Drawing Sheets

(56) References Cited

OTHER PUBLICATIONS

Ibrutinib, structure: https://www.medchemexpress.com/PCI-32765.html (Year: 2025).*

Wang et al., "Bruton's Tyrosine Kinase Inhibitors Prevent Therapeutic Escape in Breast Cancer Cells", Mol Cancer Ther., Sep. 2016, vol. 15, No. 9, pp. 2198-2208. doi:10.1158/1535-7163. MCT-15-0813.

Uckun et al., "Targeting Solid Tumors With BTK Inhibitors", Frontiers in Cell and Developmental Biology, Apr. 2021, vol. 9, Article 650414, 7 pages.

* cited by examiner

COMPOUNDS FOR THE TREATMENT AND PREVENTION OF CANCER

TECHNICAL FIELD

The present disclosure relates to methods for treating cancer (e.g. breast cancer). In particular, the compounds of Formula (I), Formula (II), Formula (III), Formula (IV) or Formula (V), or compositions thereof are employed for the treatment of cancer by inhibiting the growth and/or viability of cancer cells (e.g. breast cancer cells).

BACKGROUND

Cancer is a major health problem and is a leading cause of death worldwide. In 2020, nearly 19.3 million new cases of cancer were reported worldwide, and breast cancer was ranked at the top with 11.7% of cases. The number of new cancer cases is estimated to increase to 29.5 million new cases per year and the number of cancer-related deaths is estimated to increase to 16.4 million per year in 2040. Among females, breast cancer accounts for 36.1% of all reported malignant cancer cases. Chemotherapy can extend survival in patients diagnosed with a wide range of malignancies. However, toxic side-effects to normal cells and tissues limits chemotherapy dose intensity, frequency, and efficacy. For instance, the cardiotoxicity and nephrotoxicity associated with the widely prescribed anti-cancer drugs limit their full therapeutic potential. Consequently, developing strategies to reduce these adverse effects while maintaining or improving the efficacy of the treatment is a key goal in advancing cancer therapy.

Despite years of research into the development of new methods of treatment, many types of cancer, including, breast cancer, remain quite common. A safe and effective cancer treatment has been the goal of investigators for a substantial period of time. Successful cancer therapies must be capable of effectively targeting, eliminating, destroying, killing, and/or inhibiting the growth and/or viability of cancer cells, while avoiding severe side-effects. Therefore, there is an urgent need for an effective and safe approach for treating cancer, in particular breast cancer.

The present disclosure is directed to provide an improvement in the treatment or prevention of cancer, especially breast cancer.

SUMMARY

In accordance with the present invention, disclosed herein is a method of treating or preventing cancer in a subject in need thereof, comprising administering to the subject:

(i) a therapeutically effective amount of a compound of Formula (I):

(I)

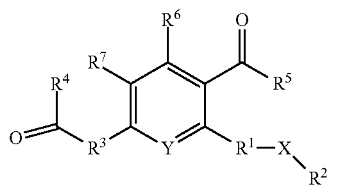

wherein:

$R^1$ is independently selected from the group consisting of optionally substituted cycloalkyl, heterocyclyl, aryl, heteroaryl; —O; —S; —$C(R)_2$, wherein R is selected from the group comprising a hydrogen, an alkyl, a haloalkyl, an alkylamino, and/or an alkoxy; —NR, wherein R is selected from the group comprising a hydrogen, an alkyl, a cycloalkyl, or a haloalkyl; or —PR, wherein R is selected from the group comprising a hydrogen, a halogen, an alkyl, a cycloalkyl, or a haloalkyl;

$R^2$ is independently selected from the group consisting of optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen; a hydrogen, halogen, cycloalkenyl, cycloalkynyl, haloalkyl, alkoxy, alkylamino, —$N(R)_2$, wherein R is selected from the group comprising a hydrogen, an alkyl, a cycloalkyl, and/or a haloalkyl; or N(HR), wherein R is selected from the group comprising a hydrogen or an alkyl;

$R^3$ is independently selected from the group consisting of optionally substituted cycloalkyl, heterocyclyl, —$C_{1-8}$ alkyl-heterocyclyl, —$C_{1-8}$ alkyl-cycloalkyl, aryl, and heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen;

$R^4$ is independently selected from the group consisting of optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, alkylamino, —$N(R)_2$, wherein R is selected from the group comprising a hydrogen, an alkyl, a cycloalkyl, and/or a haloalkyl; or N(HR), wherein R is selected from the group comprising a hydrogen or an alky;

$R^5$ is independently selected from the group consisting of —$N(R)_2$, wherein R is selected from the group comprising a hydrogen, an alkyl, a cycloalkyl, and/or a haloalkyl; N(HR), wherein R is selected from the group comprising a hydrogen or an alkyl, optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, or a alkylamino;

$R^6$ is independently selected from the group consisting of hydrogen, halogen, optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, alkylamino, —$N(R)_2$, wherein R is selected from the group comprising a hydrogen, an alkyl, a cycloalkyl, and/or a haloalkyl; or N(HR), wherein R is selected from the group comprising a hydrogen or an alkyl;

$R^7$ is independently selected from the group consisting of hydrogen, halogen, optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, $-C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, alkylamino, $-N(R)_2$, wherein R is selected from the group comprising a hydrogen, an alkyl, a cycloalkyl, and/or a haloalkyl; or N(HR), wherein R is selected from the group comprising a hydrogen or an alkyl;

X is independently selected from the group consisting of —O; —S; $-C(R)_2$, wherein R is selected from the group comprising a hydrogen, an alkyl, a cycloalkyl, a haloalkyl, an alkylamino, and/or an alkoxy; —NR, wherein R is selected from the group comprising a hydrogen, an alkyl, a cycloalkyl, or a haloalkyl; and —PR, wherein R is selected from the group comprising a hydrogen, a halogen, an alkyl, a cycloalkyl, or a haloalkyl; and Y is independently selected from N or P; or (ii) a pharmaceutically acceptable salt, co-crystal, polymorph, hydrate, solvate, prodrug, bioisostere, or a stereoisomer thereof.

In accordance with the present invention, in another aspect disclosed herein is a method of treating or preventing cancer in a subject in need thereof, comprising administering to the subject:

(i) a therapeutically effective amount of a compound of Formula (V):

(V)

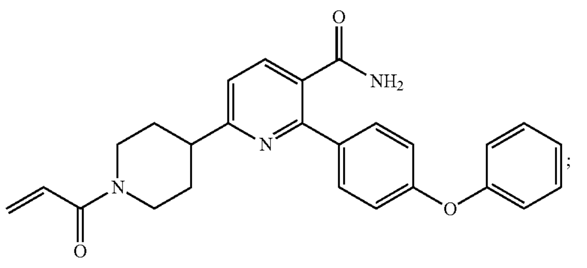

;

(ii) a pharmaceutically acceptable salt, co-crystal, polymorph, hydrate, solvate, prodrug, bioisostere, or a stereoisomer thereof.

In a preferred embodiment, the present disclosure provides a use of a compound of Formulae (I) to (V), or a pharmaceutically acceptable salt, co-crystal, polymorph, hydrate, solvate, prodrug, N-oxide, bioisostere or a stereoisomer thereof, or a composition comprising a therapeutically effective amount of the compound of Formulae (I) to (V), or a pharmaceutically acceptable salt, co-crystal, polymorph, hydrate, solvate, prodrug, or a stereoisomer thereof, for the treatment of cancer.

In another aspect, the present disclosure provides a use of a compound of Formulae (I) to (V) or a pharmaceutically acceptable salt, co-crystal, polymorph, hydrate, solvate, prodrug, N-oxide, bioisostere or a stereoisomer thereof, or a composition comprising a therapeutically effective amount of the compound of Formulae (I) to (V), or a pharmaceutically acceptable salt, co-crystal, polymorph, hydrate, solvate, prodrug, or a stereoisomer thereof, in the manufacture of a medicament for treating cancer.

In yet another aspect, provided herein are methods of treating cancer, which optionally include administering a compound of Formulae (I) to (V) in conjunction with a chemotherapeutic agent to a subject. A chemotherapeutic agent comprises any treatment applicable for cancer treatment.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DEFINITIONS

Figure 1:
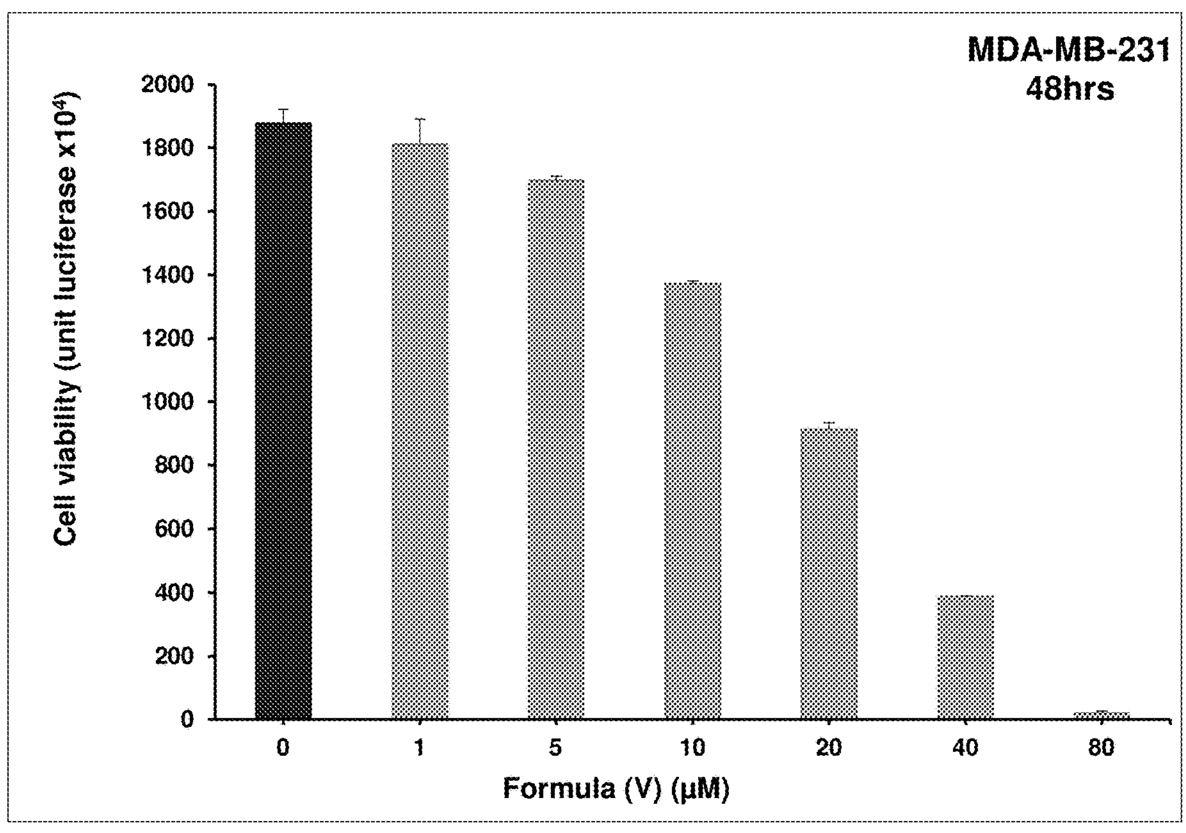
FIG. 1 depicts the cell viability assay (absolute cell viability values) on the MDA-MB-231 breast cancer cell line for the compound of Formula (V).

As used in this description and the accompanying claims, the following terms shall have the meanings indicated, unless the context otherwise requires:

As used herein, the singular forms "a", "an", and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variation thereof) "comprising", "comprises", "comprise", "consisting essentially of", "consisting", and "consists" can be used interchangeably.

The term "exemplary" is used herein to mean "serving as an example, instance, or illustration." Any embodiment described herein as "exemplary" is not necessarily to be construed as preferred or advantageous over other embodiments.

The term "bioisostere" refers to a compound or group that possesses near molecular shapes and volumes, approximately the same distribution of electrons and which exhibit similar physical properties such as hydrophobicity. Bioisostereic compounds affect the same biochemically associated systems as agonist or antagonists and thereby produce biological properties that are related to each other.

The terms "stereoisomer" or "stereoisomers" refer to any enantiomers, diastereomers or geometrical isomers of the compounds of the Formulae (I) to (V), wherever they are chiral. When the compounds of the Formulae (I) to (V) and related formulae are chiral, they can exist in racemic or in optically active form. It should be understood that the invention encompasses all stereochemical isomeric forms, including diastereomeric, enantiomeric and epimeric forms, and mixtures thereof.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the terms "comprises" or "comprising" are generally used in the sense of include, that is to say permitting the presence of one or more features or components.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as the event or circumstance where the alkyl is not substituted.

The term "pharmaceutically acceptable" means that, which is useful in preparing a pharmaceutical composition that is generally safe, non-toxic and neither biologically nor otherwise undesirable and includes that which is acceptable for veterinary as well as human pharmaceutical use. These "pharmaceutically acceptable" substances are suitable for use in interact with bodily tissues without causing excessive irritation, allergic responses, or other complications, commensurate with a reasonable benefit/risk ratio.

The term "pharmaceutically acceptable salt" refers to the salts of the compounds, that is pharmaceutically acceptable and that possesses the desired pharmacological activity of the parent compound. The pharmaceutically acceptable salts of the compounds of this disclosure include those derived from suitable inorganic and organic acids and bases. Such salts include: salts derived from inorganic bases such as Li, Na, K, Ca, Mg, Fe, Cu, Zn, Al, Mn, comprising their different oxidation states; salts of organic bases such as N,N'-diacetylethylenediamine, 2-dimethylaminoethanol, isopropylamine, morpholine, piperazine, piperidine, procaine, diethylamine, triethylamine, trimethylamine, tripropylamine, tromethamine, choline hydroxide, dicyclohexylamine, metformin, benzylamine, phenylethylamine, dialkylamine, trialkylamine, thiamine, aminopyrimidine, aminopyridine, purine, pyrimidine, spermidine, and the like; chiral bases like alkylphenylamine, glycinol, phenyl glycinol and the like, salts of natural amino acids such as glycine, alanine, valine, leucine, isoleucine, lysine, arginine, serine, threonine, phenylalanine; unnatural amino acids such as D-isomers or substituted amino acids; salts of acidic amino acids such as aspartic acid, glutamic acid; guanidine, substituted guanidine wherein the substituents are selected from nitro, amino, alkyl, alkenyl, alkynyl, ammonium or substituted ammonium salts. Salts may include acid addition salts where appropriate which are sulphates, nitrates, phosphates, perchlorates, borates, hydrohalides, acetates, tartrates, maleates, citrates, succinates, methanesulfonates, benzoates, salicylates, hydroxynaphthoates, benzenesulfonates, ascorbates, and the likes thereof.

The term "polymorph" refers to the crystallization of the same compound, which differs only in the lattice.

As used herein, the terms "prevents", "preventing", "prevention", "arresting", "blocking", "alleviating", "relieving", or "inhibits" refer to a method of preventing or inhibiting the onset of a disease and/or its attendant symptoms or barring a subject from acquiring a disease. As used herein, "prevent", "preventing", "prevention", "arresting", "blocking", "alleviating", "relieving", or "inhibiting" also include delaying the onset of a disease and/or its attendant symptoms and reducing a subject's risk of acquiring a disease.

The terms "solvate" or "solvates" refer to a complex in which the compounds of the Formulae (I) to (V) of the present disclosure are a proportional amount of solvent molecules combined. A specific solvate in which the solvent is water is referred to as a hydrate.

The term "subject" in accordance with the present invention, includes, e.g., mammals, such as dogs, cats, horses, rats, mice, monkeys, and humans.

The terms "therapeutically effective amount" or "effective amount" refer to the quantity of the compound of the Formulae (I) to (V) disclosed herein that (i) treats or prevents a specific disease, disorder, or condition or syndrome; (ii) reduces, improves, or eliminates one or more symptoms associated with the disease, disorder, or syndrome; or (iii) delays the onset of one or more symptoms of the disease, disorder, or syndrome described herein. In cases of cancer, the therapeutically effective amount of the drug may reduce cancer cell proliferation, shrink tumor size, inhibit cancer cell migration to peripheral organs, suppress tumor metastasis, slow tumor growth to some extent, and/or alleviate one or more symptoms associated with cancer.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal. In an embodiment, a prodrug has less than 10 percent activity relative to the free or active drug derived or released therefrom. In an embodiment, a prodrug has less than 5 percent activity relative to the free or active drug derived or released therefrom. In an embodiment, a prodrug has less than 1 percent activity relative to the free or active drug derived or released therefrom.

The terms "—NR", "—PR", "—C(R2)", "—N(R)2", "—CON(R)2", "—CONHR", or "—PO(OR)2 refer to one or two R groups attached to a carbon, nitrogen phosphorus, oxygen, or sulfur atom, for example "—CON(R)2" refers to two R group attached to a Nitrogen, as shown in the formula below:

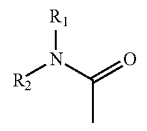

The terms "—S", "—N", "—O", "—P" refer to a sulfur, nitrogen, oxygen, or phosphorus atom, and may include the forms "—S—", "—N—", "—O—", "—P—", "—P═", "—N═" where applicable due to formula structure requirements.

The term "substituted" as used herein refers to substitution with at least one substituent with, for example, an alkyl group, an alkenyl group, and an alkynyl group, a cycloalkyl group and aryl group As used herein, the term "($C_a$-$C_b$)" wherein a and b are integers refers to a straight or branched chain alkyl radical having from a to b carbon atoms. For example, when a is 1 and b is 6, the term includes methyl, ethyl, n-propyl, isopropyl, n-butyl, isobutyl, sec-butyl, t-butyl, n-pentyl and n-hexyl.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "carbocyclic" refers to a cyclic radical whose ring atoms are all carbon, and includes aryl, cycloalkyl, and cycloalkenyl radicals.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular refers to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

The recitation of a listing of chemical groups in any definition of a variable herein includes definitions of that variable as any single group or combinations of listed groups. The recitation of an embodiment for a variable or aspect herein includes that embodiment as any single embodiment or in combination with any other embodiments or portions thereof.

Unless defined otherwise, all technical and scientific terms used herein have the same meaning as commonly understood by one of ordinary skill in the art to which the disclosure belongs. Although any methods and materials like or equivalent to those described herein may be used in the practice or testing of the present disclosure, the preferred materials and methods are described below.

DETAILED DESCRIPTION

The present invention pertains to a method of treating cancer in a subject in need thereof, comprising a compound of Formula (I), structurally represented as follows:

(i) Formula (I):

(I)

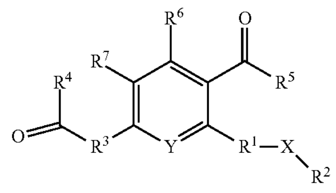

wherein:

- $R^1$ is independently selected from the group consisting of optionally substituted cycloalkyl, heterocyclyl, aryl, heteroaryl; —O; —S; —C(R)$_2$, wherein R is selected from the group comprising a hydrogen, an alkyl, a haloalkyl, an alkylamino, and/or an alkoxy; —NR, wherein R is selected from the group comprising a hydrogen, an alkyl, a cycloalkyl, or a haloalkyl; or —PR, wherein R is selected from the group comprising a hydrogen, a halogen, an alkyl, a cycloalkyl, or a haloalkyl;
- $R^2$ is independently selected from the group consisting of optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen; a hydrogen, halogen, cycloalkenyl, cycloalkynyl, haloalkyl, alkoxy, alkylamino, —N(R)$_2$, wherein R is selected from the group comprising a hydrogen, an alkyl, a cycloalkyl, and/or a haloalkyl; or N(HR), wherein R is selected from the group comprising a hydrogen or an alkyl;
- $R^3$ is independently selected from the group consisting of optionally substituted cycloalkyl, heterocyclyl, —$C_{1-8}$ alkyl-heterocyclyl, —$C_{1-8}$ alkyl-cycloalkyl, aryl, and heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen;
- $R^4$ is independently selected from the group consisting of optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, alkylamino, —N(R)$_2$, wherein R is selected from the group comprising a hydrogen, an alkyl, a cycloalkyl, and/or a haloalkyl; or N(HR), wherein R is selected from the group comprising a hydrogen or an alkyl,
- $R^5$ is independently selected from the group consisting of —N(R)$_2$, wherein R is selected from the group comprising a hydrogen, an alkyl, a cycloalkyl, and/or a haloalkyl; N(HR), wherein R is selected from the group comprising a hydrogen or an alkyl, optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, or a alkylamino;

$R^6$ is independently selected from the group consisting of hydrogen, halogen, optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, alkylamino, —$N(R)_2$, wherein R is selected from the group comprising a hydrogen, an alkyl, a cycloalkyl, and/or a haloalkyl; or N(HR), wherein R is selected from the group comprising a hydrogen or an alkyl;

$R^7$ is independently selected from the group consisting of hydrogen, halogen, optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, alkylamino, —$N(R)_2$, wherein R is selected from the group comprising a hydrogen, an alkyl, a cycloalkyl, and/or a haloalkyl; or N(HR), wherein R is selected from the group comprising a hydrogen or an alkyl;

X is independently selected from the group consisting of —O; —S; —$C(R)_2$, wherein R is selected from the group comprising a hydrogen, an alkyl, a cycloalkyl, a haloalkyl, an alkylamino, and/or an alkoxy; —NR, wherein R is selected from the group comprising a hydrogen, an alkyl, a cycloalkyl, or a haloalkyl; and —PR, wherein R is selected from the group comprising a hydrogen, a halogen, an alkyl, a cycloalkyl, or a haloalkyl; and Y is independently selected from N or P; or a pharmaceutically acceptable salt, co-crystal, polymorph, hydrate, solvate, prodrug, bioisostere, or a stereoisomer thereof.

In one aspect, the present invention discloses a method of treating or preventing cancer in a subject in need thereof, comprising administering to the subject a therapeutically effective amount of a composition comprising a therapeutically effective amount of the compound of Formula (I), or a pharmaceutically acceptable salt, co-crystal, polymorph, hydrate, solvate, prodrug, or a stereoisomer thereof, and one or more pharmaceutical excipients and/or carriers.

In some embodiments, the present invention pertains to a method comprising administering one or more additional therapeutic agents, wherein the additional therapeutic agents are administered prior to, concurrently with, or subsequently to the administration of the compound of Formula (I) or the composition comprising the compound of Formula (I).

In a preferred embodiment, the present invention pertains to a method of treating cancer in a subject in need thereof, comprising a compound of Formula (II), structurally represented as follows:

(i) Formula (II):

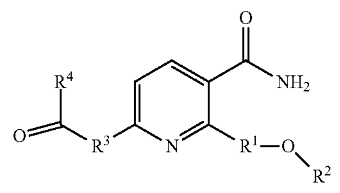

(II)

wherein:

$R^1$ is independently selected from the group consisting of optionally substituted cycloalkyl, heterocyclyl, aryl, heteroaryl; —O; —S; —$C(R)_2$, wherein R is selected from the group comprising a hydrogen, an alkyl, a haloalkyl, an alkylamino, and/or an alkoxy; —NR, wherein R is selected from the group comprising a hydrogen, an alkyl, a cycloalkyl, or a haloalkyl; or —PR, wherein R is selected from the group comprising a hydrogen, a halogen, an alkyl, a cycloalkyl, or a haloalkyl;

$R^2$ is independently selected from the group consisting of optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen; a hydrogen, halogen, cycloalkenyl, cycloalkynyl, haloalkyl, alkoxy, alkylamino, —$N(R)_2$, wherein R is selected from the group comprising a hydrogen, an alkyl, a cycloalkyl, and/or a haloalkyl; or N(HR), wherein R is selected from the group comprising a hydrogen or an alkyl;

$R^3$ is independently selected from the group consisting of optionally substituted cycloalkyl, heterocyclyl, —$C_{1-8}$ alkyl-heterocyclyl, —$C_{1-8}$ alkyl-cycloalkyl, aryl, and heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen;

$R^4$ is independently selected from the group consisting of optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, alkylamino, —$N(R)_2$, wherein R is selected from the group comprising a hydrogen, an alkyl, a cycloalkyl, and/or a haloalkyl; or N(HR), wherein R is selected from the group comprising a hydrogen or an alkyl; or (ii) a pharmaceutically acceptable salt, co-crystal, polymorph, hydrate, solvate, prodrug, bioisostere, or a stereoisomer thereof.

In some embodiments, for a compound of Formula (II):

$R^1$ and $R^2$ are each independently selected from the group consisting of optionally substituted cycloalkyl, heterocyclyl, aryl, or heteroaryl;

$R^3$ is independently selected from the group consisting of optionally substituted cycloalkyl, heterocyclyl, —$C_{1-8}$ alkyl-heterocyclyl, —$C_{1-8}$ alkyl-cycloalkyl, aryl, and heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen; and $R^4$ is independently selected from the group consisting of optionally substituted $C_{1-8}$alkyl, —$C_{2-8}$alkenyl, —$C_{2-8}$alkynyl, cycloalkyl, heterocyclyl, aryl, or heteroaryl, wherein the heterocyclyl, —$C_{1-8}$alkyl-heterocyclyl, and heteroaryl are each 3- to 7-membered comprising 1 or 2 heteroatoms selected from nitrogen and oxygen.

In some embodiments, the method of treating or preventing cancer in a subject in need thereof, comprises administering to the subject a therapeutically effective amount of a composition comprising a therapeutically effective amount of the compound of Formula (II), or a pharmaceutically acceptable salt, co-crystal, polymorph, hydrate, solvate, prodrug, or a stereoisomer thereof, and one or more pharmaceutical excipients and/or carriers.

In some embodiments, the present invention pertains to a method comprising administering one or more additional therapeutic agents, wherein the additional therapeutic agents are administered prior to, concurrently with, or subsequently to the administration of the compound of Formula (II) or the composition comprising the compound of Formula (II).

In a preferred embodiment, the present invention pertains to a method of treating cancer in a subject in need thereof, comprising a compound of Formula (III), structurally represented as follows:

(i) Formula (III):

(III)

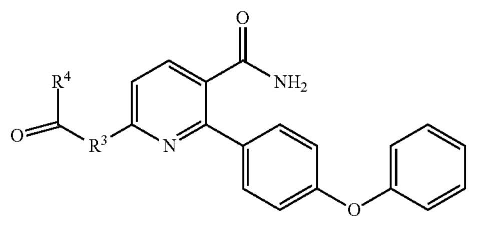

wherein $R^3$ is independently selected from the group consisting of optionally substituted cycloalkyl, heterocyclyl, —$C_{1-8}$ alkyl-heterocyclyl, —$C_{1-8}$ alkyl-cycloalkyl, aryl, and heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen;

$R^4$ is independently selected from the group consisting of optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, alkylamino, —$N(R)_2$, wherein R is selected from the group comprising a hydrogen, an alkyl, a cycloalkyl, and/or a haloalkyl; or N(HR), wherein R is selected from the group comprising a hydrogen or an alkyl; or (ii) a pharmaceutically acceptable salt, co-crystal, polymorph, hydrate, solvate, prodrug, bioisostere, or a stereoisomer thereof.

In some embodiments, the method of treating or preventing cancer in a subject in need thereof, comprises administering to the subject a therapeutically effective amount of a composition comprising a therapeutically effective amount of the compound of Formula (III), or a pharmaceutically acceptable salt, co-crystal, polymorph, hydrate, solvate, prodrug, or a stereoisomer thereof, and one or more pharmaceutical excipients and/or carriers.

In some embodiments, the present invention pertains to a method comprising administering one or more additional therapeutic agents, wherein the additional therapeutic agents are administered prior to, concurrently with, or subsequently to the administration of the compound of Formula (III) or the composition comprising the compound of Formula (III).

In some embodiments, for a compound of Formula (III):

$R^3$ is independently selected from the group consisting of optionally substituted cycloalkyl, heterocyclyl, —$C_{1-8}$alkyl-heterocyclyl, —$C_{1-8}$alkyl-cycloalkyl, aryl, and heteroaryl, wherein the heterocyclyl, —$C_{1-8}$alkyl-heterocyclyl, and heteroaryl are each 3- to 7-membered comprising 1 or 2 heteroatoms selected from nitrogen and oxygen; and $R^4$ is independently selected from the group consisting of optionally substituted $C_{1-8}$ alkyl, —$C_{2-8}$alkenyl, or —$C_{2-8}$alkynyl.

In a preferred embodiment, the present invention pertains to a method of treating cancer in a subject in need thereof, comprising a compound of Formula (IV), structurally represented as follows:

(i) Formula (IV):

(IV)

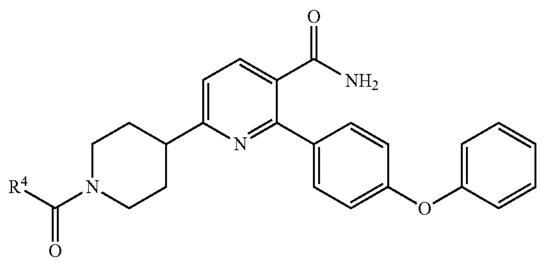

wherein $R^4$ is independently selected from the group consisting of optionally substituted $C_{1-8}$ alkyl, —$C_{2-8}$ alkenyl, —$C_{2-8}$ alkynyl, cycloalkyl, heterocyclyl, aryl, or heteroaryl, wherein the heterocyclyl, —$C_{1-8}$ alkyl-heterocyclyl, and heteroaryl are each 3- to 7-membered comprising 1 or 2 heteroatoms selected from nitrogen and oxygen, hydrogen, halogen, cycloalkenyl, cycloalkynyl, haloalkyl, alkoxy, alkylamino, —$N(R)_2$, wherein R is selected from the group comprising a hydrogen, an alkyl, a cycloalkyl, and/or a haloalkyl; or N(HR), wherein R is selected from the group comprising a hydrogen or an alkyl; or (ii) a pharmaceutically acceptable salt, co-crystal, polymorph, hydrate, solvate, prodrug, bioisostere, or a stereoisomer thereof.

In some embodiments, the method of treating or preventing cancer in a subject in need thereof, comprises administering to the subject a therapeutically effective amount of a composition comprising a therapeutically effective amount of the compound of Formula (IV), or a pharmaceutically acceptable salt, co-crystal, polymorph, hydrate, solvate, prodrug, or a stereoisomer thereof, and one or more pharmaceutical excipients and/or carriers.

In some embodiments, the present invention pertains to a method comprising administering one or more additional therapeutic agents, wherein the additional therapeutic agents are administered prior to, concurrently with, or subsequently to the administration of the compound of Formula (IV) or the composition comprising the compound of Formula (IV).

In some embodiments, for a compound of Formula (IV): $R^4$ is independently selected from the group consisting of optionally substituted $C_{1-8}$ alkyl, $—C_{2-8}$alkenyl, or $—C_{2-8}$alkynyl.

In a preferred embodiment, the present invention pertains to a method of treating cancer in a subject in need thereof, comprising a compound of Formula (V), structurally represented as follows:

(i) Formula (V):

(V)

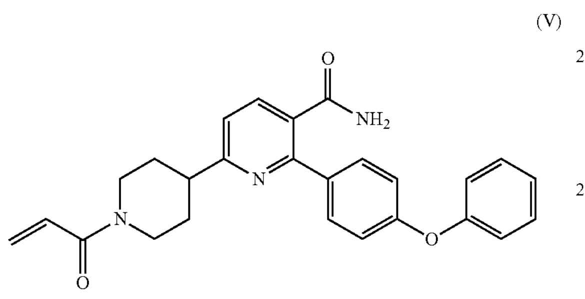

or (ii) a pharmaceutically acceptable salt, co-crystal, polymorph, hydrate, solvate, prodrug, bioisostere, or a stereoisomer thereof.

In some embodiments, the method of treating or preventing cancer in a subject in need thereof, comprises administering to the subject a therapeutically effective amount of a composition comprising a therapeutically effective amount of the compound of Formula (V), or a pharmaceutically acceptable salt, co-crystal, polymorph, hydrate, solvate, prodrug, or a stereoisomer thereof, and one or more pharmaceutical excipients and/or carriers.

In a preferred embodiment, the present invention pertains to a method comprising administering one or more additional therapeutic agents, wherein the additional therapeutic agents are administered prior to, concurrently with, or subsequently to the administration of the compound of Formula (V) or the composition comprising the compound of Formula (V).

In some embodiments, the composition is used for treating cancer. In alternative embodiments, the composition is used for preventing cancer.

In an embodiment, the cancer includes, but not limited to: Adenocarcinoma of the Colon; Adenocarcinoma of the Esophagus; Adenocarcinoma of the Lung; Adenocarcinoma of the Prostate; Adenocarcinoma of the Rectum; Advanced Adult Primary Liver Cancer; Advanced Non-Nasopharyngeal Head and Neck Carcinoma; Anaplastic Astrocytoma; Anaplastic Oligodendroglima; Anaplastic Thyroid Cancer; Bladder Cancer; Brain Tumor; Breast Cancer; Breast Cancer in Situ; Breast Neoplasms; Bronchoalveolar Cell Lung Cancer; Cancer of the Fallopian Tube; Carcinoma, Squamous Cell; Cervix Neoplasms; Colon Cancer; Colorectal Cancer; Epithelial Mesothelioma; Esophageal Cancer; Esophagogastric Cancer; Follicular Thyroid Cancer; Gastric Cancer; Gastrinoma; Gastrointestinal Carcinoid; Giant Cell Glioblastoma; Glioblastoma; Glioblastoma Multiforme; Head and Neck Cancer; Hepatocellular Carcinoma; Hypopharyngeal Cancer; Inoperable Locally Advanced Squamous Cell Carcinoma of Head and Neck; Insulinoma; Intraductal Breast Carcinoma; Islet Cell Carcinoma; Large Cell Lung Cancer; Laryngeal Cancer; Lip and Oral Cavity Cancer; Lip Cancer; Liver Cancer; Lung Adenocarcinoma With Bronchiole-Alveolar Feature; Lung Cancer; Male Breast Cancer; Medullary Thyrod Cancer; Meningeal Tumors; Metastatic Colorectal Cancer; Metastatic Gastrointestinal Carcinoid Tumor; Metastatic Pancreatic Carcinoma; Mixed Gliomas; Myelogenous Leukemia, Acute; Nasopharyngeal Carcinoma; Neuroblastoma; Non-Metastatic (T2-T4, N0-N3, MO; Stages II and III) and Histologically-Confirmed Intestinal GC; Non-Metastatic Prostate Cancer; Nonresectable Adrenocortical Carcinoma; Non-Small Cell Lung Cancer; Nose Cancer; Oligodendroglial Tumors; Oral Cancer; Oropharyngeal Cancer; Osteosarcoma; Ovarian Cancer; Ovarian Neoplasms; Pancreatic Cancer; Papillary Thyroid Cancer; Peritoneal Carcinoma; Pharynx Cancer; Pneumonic-Type Adenocarcinoma (P-ADC); Primary Hepatocellular Carcinoma; Prostate Cancer; Rectal Cancer; Recurrent Adult Primary Liver Cancer; Recurrent Breast Cancer; Recurrent Colon Cancer; Recurrent Endometrial Cancer, Recurrent Esophageal Cancer; Recurrent Glioblastoma; Recurrent Rectal Cancer; Recurrent Skin Cancer; Refractory Germ Cell Tumors Expressing EGRF; Renal Cell Cancer; Rhabdomyosarcomas; Sarcomatous Mesothelioma; Skin Cancer; Soft Tissue Sarcoma; Squamous Cell Carcinoma of the Esophagus; Squamous Cell Carcinoma of the Head and Neck; Squamous Cell Carcinoma of the Skin; Squamous Cell Lung Cancer; Stage II Esophageal Cancer; Stage III Esophageal Cancer, Synovial Sarcoma; Thorax and Respiratory Cancer; Throat Cancer; Thyroid Cancer; Transitional Cell Cancer of the Renal Pelvis and Ureter; Transitional Cell Carcinoma of the Bladder; Tubal Carcinoma; Unspecified Childhood Solid Tumor; Untreated Childhood Brain Stem Glioma; Urethral Cancer.

In a preferred embodiment the cancer is breast cancer.

In an embodiment, the composition further comprises a pharmaceutically acceptable carrier or excipient.

In any of the preceding embodiments, the method of treating or preventing cancer comprises optionally administering an additional therapeutic agent.

In one embodiment, the additional therapeutic agent is administered prior to, concurrently with, or subsequently to the administration of the compound of Formulae (I) to (V) (e.g. a compound of Formula (V)) or the composition comprising the compound of Formulae (I) to (V) (e.g. a compound of Formula (V)). In another embodiment, the additional therapeutic agent is administered prior to the administration of the compound of Formulae (I) to (V) (e.g. a compound of Formula (V)) or the composition comprising the compound of Formulae (I) to (V) (e.g. a compound of Formula (V)). In a further embodiment, the additional therapeutic agent is administered concurrently with the administration of the compound of Formulae (I) to (V) (e.g. a compound of Formula (V)) or the composition comprising the compound of Formulae (I) to (V) (e.g. a compound of Formula (V)). In yet another embodiment, the additional therapeutic agent is administered subsequent to the administration of the compound of Formulae (I) to (V) (e.g. a compound of Formula (V)) or the composition comprising the compound of Formulae (I) to (V) (e.g. a compound of Formula (V)).

In an embodiment, the compound of Formulae (I) to (V) (e.g. a compound of Formula (V)) exhibits therapeutic effect by targeting blocking the growth and/or viability of cancer such as breast cancer. In an embodiment, it has a similar or more inhibitory effect compared to agents that have been studied for their anti-cancer effects.

Thus, in an embodiment, the compounds of the present invention kill about more than 70% of cancer cells. In an embodiment, the compounds of the present invention kills about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of cancer cells.

In an alternative embodiment, the compounds of the present invention kill about at least 50% of cancer cells. For example, the compounds of the present invention may kill about at least 60%, at least 70%, at least 80% or at least 90% of cancer cells.

The compositions and methods of the present disclosure are utilized to treat a subject in need thereof. In certain embodiments, the subject is a mammal such as a human or a non-human mammal. When administered to an animal, such as a human, the composition or the compound is preferably administered as a pharmaceutical composition comprising, for example, the compounds of the present invention and a pharmaceutically acceptable carrier. Pharmaceutically acceptable carriers are well known in the art and include, for example, aqueous solutions such as water or physiologically buffered saline or other solvents or vehicles such as glycols, glycerol, and oils such as olive oil or injectable organic esters.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free or substantially pyrogen-free.

The phrase "pharmaceutically acceptable carrier" as used herein means a pharmaceutically acceptable material, composition, or vehicle, such as a liquid or solid filler, diluent, excipient, solvent, or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The excipients can be chosen, for example, to effect delayed release of an agent or to selectively target one or more cells, tissues, or organs.

The pharmaceutical composition may be formulated as tablets, pills, powders, granules, capsules, suspensions, liquids for internal use, emulsions, syrups, aerosols, or sterile injectable solutions. Depending on the intended use, the composition can be administered to a subject by any of a number of routes of administration including, for example orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin or as an eye drop). The compound may also be formulated for inhalation. In yet another embodiment, the compound may be simply dissolved or suspended in sterile water.

The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be the amount of the compound which produces a therapeutic effect. Generally, out of one hundred percent, this amount will range from about 1 percent to about ninety-nine percent of active ingredients, preferably from about 5 percent to about 70 percent, most preferably from about 10 percent to about 30 percent.

Methods of preparing these formulations or compositions include the step of bringing into association an active compound, such as the compounds of the present invention with the carrier and, optionally, one or more accessory ingredients. In general, the formulations are prepared by uniformly and intimately bringing into association a compound of the present disclosure with liquid carriers or finely divided solid carriers or both and then, if necessary, shaping the product.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound and, if desired, another type of therapeutic agent being administered with the compound of the disclosure. A larger total dose can be delivered by multiple administrations of the agent. Methods to determine efficacy and dosage are known to those skilled in the art.

In general, a suitable daily dose of an active compound used in the compositions and methods of the disclosure will be that amount of the compound that is the lowest dose effective to produce a therapeutic effect. Such an effective dose will generally depend upon the factors described above.

As anticipated above, the compounds may be administered by any appropriate route, for example orally, parenterally, topically, or rectally. It will be appreciated that the preferred route may vary with, for example, the condition of the recipient of the compound and the cancer to be treated. In certain embodiments, the extract may be especially suitable for the preparation of pharmaceuticals for intravenous administration, such as intravenous injection or infusion, provided that it does not contain components with serum-precipitating and/or haemagglutinating properties which disturb such an application. The extract may therefore be provided in the form of ampoule preparations which are directed to intravenous administration. In still other embodiments, the method comprises systemic administration of a subject composition to a subject.

Also provided are methods of treating cancer, which optionally include administering the compounds in conjunction with a chemotherapeutic agent to a subject. Conjunctive therapy includes sequential, simultaneous and separate, or co-administration of the compound and the chemotherapeutic agent in a way that the therapeutic effect of the chemotherapeutic agent is not entirely disappeared when the compound is administered. In certain embodiments, compound and the chemotherapeutic agent may be compounded together in the same unitary pharmaceutical composition including both entities. Alternatively, the combination of compound and chemotherapeutic agent may be administered separately in separate pharmaceutical compositions, each including one of the compound and chemotherapeutic agent in a sequential manner wherein, for example, the compound or the chemotherapeutic agent is administered first and the other second. A chemotherapeutic agent comprises any treatment applicable for cancer treatment.

Exemplary doses of the compounds range from about 0.001, 0.01, 0.1, 0.5, 1, 2, 3, 4, 5, 6, 7, 8, 9, 10, 11, 12, 13, 14, 15, 16, 17, 18, 19, 20, 25, 30, 40, 50, 60, 70, 80, 90, 100, 120, 130, 140, 150, 160, 170, 180, 190, 200, 250, 300, 350, 400, 450 μM to about 500 μM. In an embodiment, the dose is about 10, 11, 12, 13, 14, 15, 16, 17, 18, 19, 20, 25, 30, 40 to about 50 μM, preferably about 15 to about 25 μM or about 20 μM.

Exemplary doses of the compounds range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of the compound will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg/day to about 250 mg/day per kg. In a further embodiment, the dose in the range of about 100 mg/day to about 200 mg/day per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

If desired, the effective daily dose of the active compound may be administered as one, two, three, four, five, six or more sub-doses administered separately at appropriate intervals throughout the day, optionally, in unit dosage forms. In yet another embodiment of the present disclosure, the active compound may be administered two or three times daily. In preferred embodiments, the active compound will be administered once daily.

The combined use of a compound of Formulae (I) to (V) (e.g. a compound of Formula (V)) and other chemotherapeutic agents may reduce the required dosage for any individual component because the onset and duration of effect of the different components may be complementary. In such combination therapies, the different active agents may be delivered together or separately, and simultaneously or at different times within the day. The patient receiving this treatment is any mammal in need, including primates, in particular humans.

Wetting agents, emulsifiers, and lubricants, such as sodium lauryl sulfate and magnesium stearate, as well as coloring agents, coating agents, release agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol and the like; and (3) metal-chelating agents, such as citric acid, ethylenediamine tetraacetic acid (EDTA), sorbitol, tartaric acid, phosphoric acid and the like.

In certain embodiments, the compounds of the present invention can be formulated and administered in a prodrug form. A prodrug is generally defined as a biologically inactive derivative of a parent drug molecule, which is activated by a chemical or enzymatic transformation within the body, which, in the process, involves the release of the active drug. In general, prodrugs comprise functional derivatives of the claimed compounds, which are capable of being enzymatically activated or converted into the more active parent form. Thus, in the treatment methods of the present disclosure, the term "administering" encompasses the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described. The the compounds of the present invention may be obtained from commercial sources or can be prepared by the conventional methods known in the art.

The present disclosure now being generally described, it will be more readily understood by reference to the following examples, which are included merely for purposes of illustration of certain aspects and embodiments of the present disclosure and are not intended to limit the present disclosure in any way.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

EXAMPLES

Example 1

The ability of the compound of Formula (V) to inhibit breast cancer cell growth and/or viability was analyzed based on the MDA-MB-231 breast cancer cell line and the T47D breast cancer cell line.

Human triple-negative breast cancer (TNBC) cells MDA-MB-231 and human breast cancer cell T47D were used. All media were supplemented with 1% penicillin-streptomycin and 10% of fetal bovine serum. All cell lines were incubated at 37° C. Culturing media were replaced every three days, and the cells were passed once weekly, upon reaching 90 to 95% confluence.

For the cell viability assay, MDA-MB-231 and T47D cell lines were seeded in 96-well plates at a density of 5000 cells per well. After 24 hours of incubation, cells were treated with an increasing concentration of the compound of Formula (V) (1, 5, 10, 20, 40, and 80 μM) in duplicates for 48 hours, while the triplicate control wells were treated with equal amounts of the medium with DMSO 0.1%. The compounds effect on the cell viability of tested cell lines was determined using a Luminescent Cell Viability Assay. The measured ATP in each condition reflects the metabolically active cells. Cell viability was expressed in absolute values and/or as a percentage (%) by comparing the viability of the compound-treated cells to that of control cells, which were assumed to be 100% viable.

For the caspase 3/7 activity, cells were seeded at a density of 5000 cells/well into 96-well plate and treated with the compound of Formula (V) (10, 20, 40, and 80 μM) for 48 h, in duplicates. Control cells were exposed to 0.1% DMSO. Caspase 3/7 activity was measured using a luminescent Caspase-Glo 3/7 assay kit. Caspase 3/7 activity was normalized to the cellular viability and expressed as fold changes.

For the colony growth assay, MDA-MB-231 and T47D cells were seeded in 6-well plates at densities of 100 cells/well while A549 was seeded at the density of 50 cells/well. Plates were then kept in a humidified incubator at 37° C. for 7 days, allowing colony formation. Formed colonies were treated in duplicates with increasing concentrations of the compound of Formula (V) (10, 20, 40, and 80 μM), every 3 days, up to 10 days for the MDA-MB-231 and T47D cell lines. Control wells were treated with a similar volume of medium. On the stopping day, colonies were stained using 0.5% crystal violet. Colonies containing 50 or more cells were enumerated using an inverted microscope. The experimental data were represented as absolute values or as colony percentage (%), by comparing drug-treated colonies to control colonies, which were considered as 100%.

Cancer cell viability, in the presence or absence of the compound, was measured in the cell lines. The cell viability assay helps to determine the number of healthy viable cells in response to various concentrations of the compound assessing its anticancer potential. This test helps assess the effects of the efficacy of the compound as a therapeutic compound. The $IC_{50}$ is the concentration at which the drug reduces cell growth by 50% compared to an untreated control. A lower $IC_{50}$ indicates higher potency, meaning less of the compound is needed to achieve half-maximal inhibition.

Figure 2:
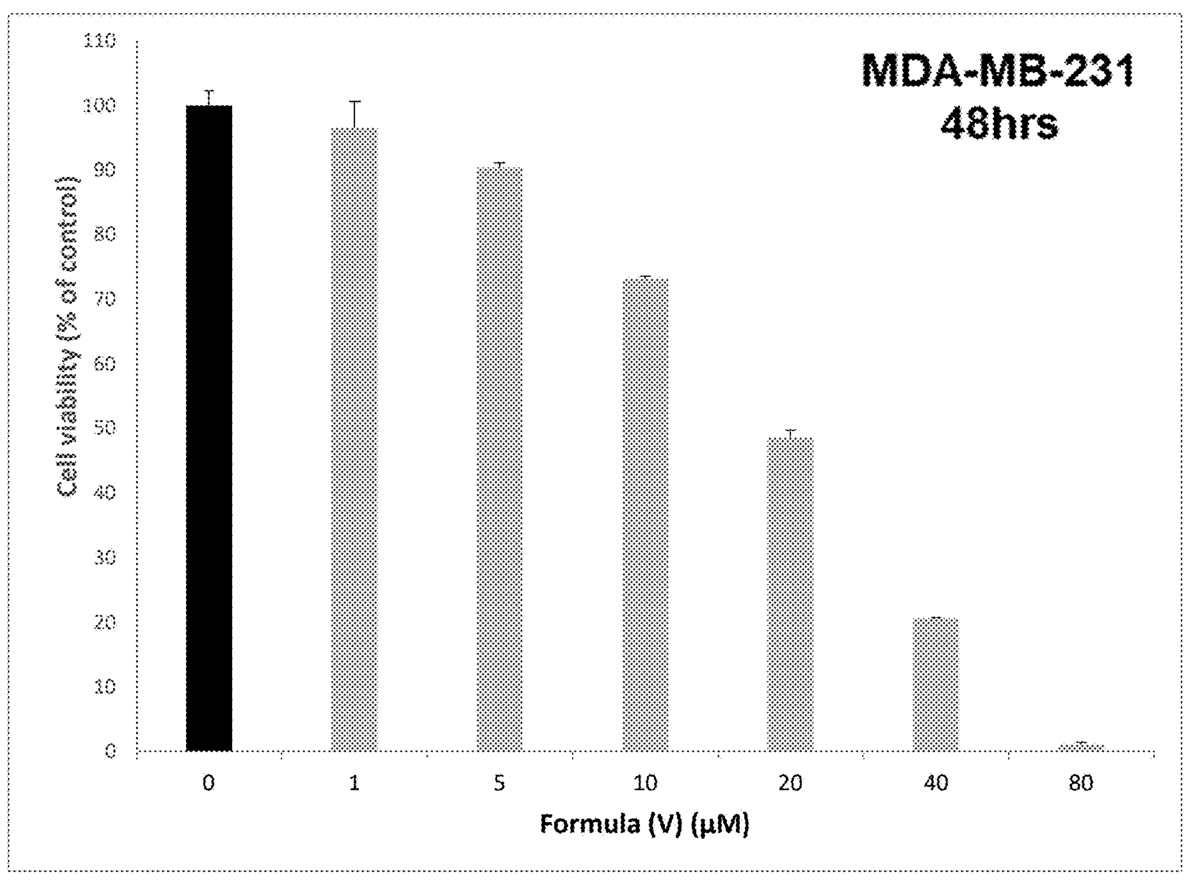
FIG. 2 depicts the cell viability assay (as a percentage relative to the untreated control (at 0 μM)) on the MDA-MB-231 breast cancer cell line for the compound of Formula (V).

FIGS. 1 and 2 depict the cell viability assay on the MDA-MB-231 breast cancer cell line following 48 hours of treatment with various concentrations of for the compound of Formula (V). FIG. 1 displays the absolute cell viability values, while FIG. 2 represents cell viability as a percentage relative to the untreated control (at 0 μM). For FIG. 2, 100% is equivalent to $1877.27\times10^4$ luciferase units. The results, at different concentrations, are compared with respect to the untreated control (at 0 μM). The results show a concentration-dependent reduction in cell viability. At 20 μM, cell viability decreased to 48.6±2% (equivalent to $912.99\times10^4$ luciferase units; the standard deviations are from repeated reads done per experiment), indicating that the $IC_{50}$ is 20 μM. At 80 μM, cell viability was reduced to 1%, corresponding to a 99% inhibition. These findings highlight the significant inhibitory effect of the compound of Formula (V) on cell viability in MDA-MB-231 cells.

Caspase-3 and caspase-7 are key enzymes involved in the process of apoptosis, or programmed cell death. A fold increase in caspase 3/7 activity typically signals that apoptosis contributed to the decrease in cell viability (as depicted in FIGS. 1 and 2).

Figure 3:
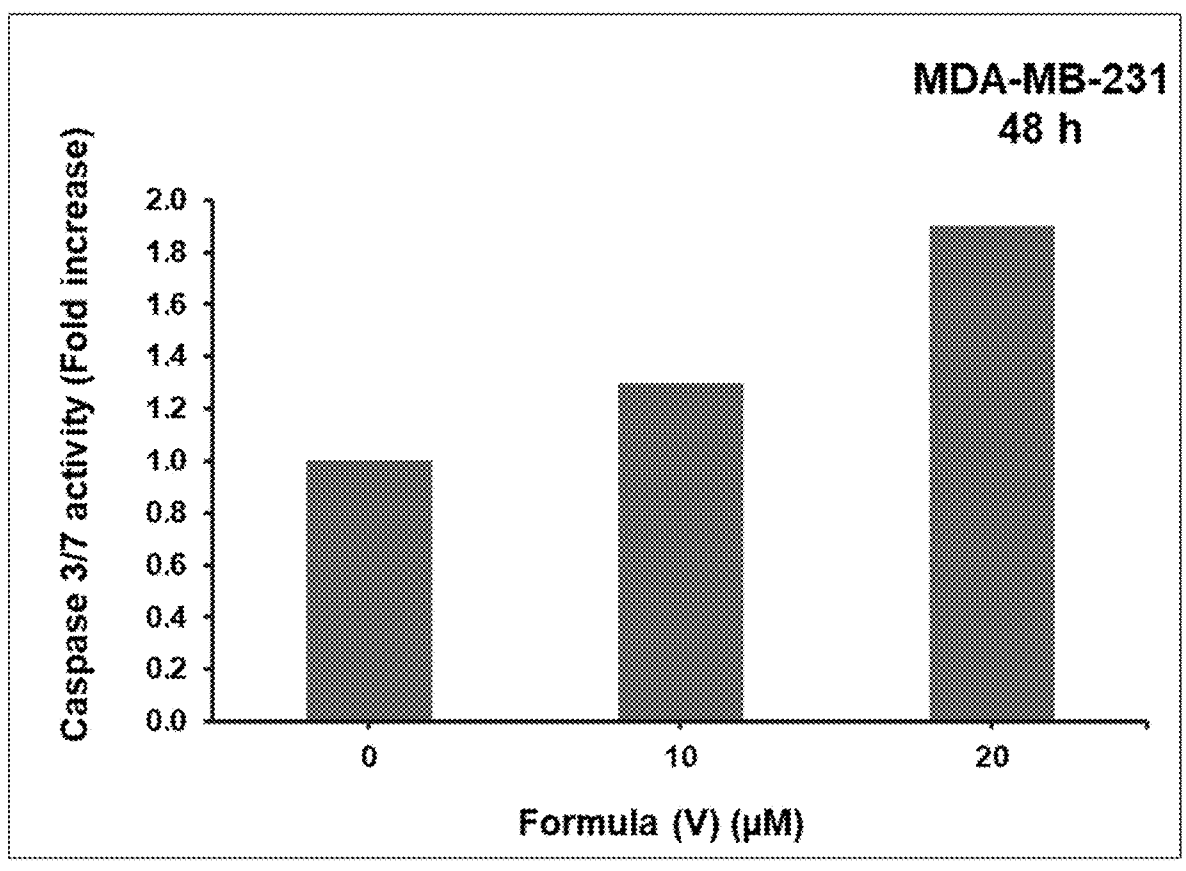
FIG. 3 depicts the caspase 3/7 activity on the MDA-MB-231 breast cancer cell line or the compound of Formula (V).

FIG. 3 depicts the caspase 3/7 activity on the MDA-MB-231 breast cancer cell line or the compound of Formula (V). The caspase 3/7 activity is measured and reported as a "fold increase". In other words, the graph shows the relative change in the caspase 3/7 activity level compared to the baseline control condition. FIG. 3 demonstrates the fold increase in caspase 3/7 activity after 48 hours treatment of the MDA-MB-231 cell line with the compound at two different concentrations relative to the drug-free control baseline (at 0 μM). At a concentration of 20 μM, the caspase 3/7 activity shows a 2-fold increase compared to the baseline. As caspase 3/7 activation is a hallmark of apoptosis, this indicates that the reduction in cell viability induced by the compound is primarily due to the apoptotic cell death of the MDA-MB-231 cells.

The colony growth assay demonstrates the impact of a drug on the growth of pre-established colonies (a group of more than 50 cells). The test is helpful for assessing the long-term effects of treatments on cancer cell survival, as it measures the ability of the compound to kill tumor cells or inhibit their ability to reproduce. This test is indicative of the therapy effectiveness and potential resistance mechanisms.

Table 1 below presents the average number of colonies in the MDA-MB-231 cell line from duplicates. It includes results of the untreated control and the treatments with the compound of Formula (V) at concentrations of 0 μM (i.e. control), 10 μM and 20 μM. Additionally, the table shows the reduction in colony number compared to the untreated control-colony.

TABLE 1 average number of colonies in the MDA-MB-231 cell line with the compound of Formula (V) at concentrations of 0 μM (i.e. control), 10 μM and 20 μM.

| (μM) | Number of Colonies | % of inhibition |
|---|---|---|
| 0 | 117 | — |
| 10 | 94 | 20 |
| 20 | 70 | 41 |

Figure 4:
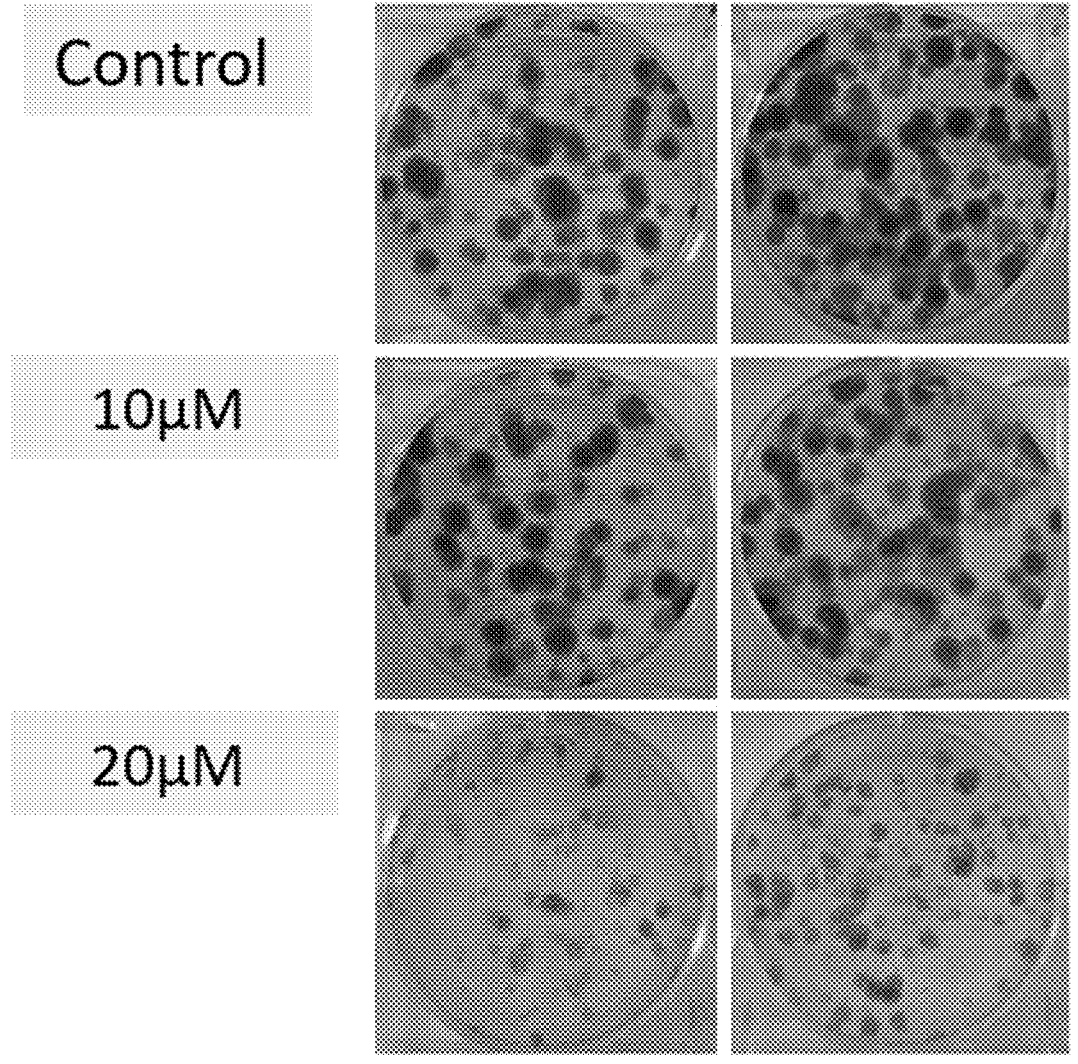
FIG. 4 sets out images showing the MDA-MB-231 colonies at various micro-molar concentrations of the compound of Formula (V).

FIG. 4 sets out images showing the MDA-MB-231 colonies at various micro-molar concentrations of the compound of Formula (V). The images show the MDA-MB-231 colonies, in duplicates (one to the left and one to the right), at 0 μM (i.e. control), 10 μM, and 20 μM of the compound. These images show the reduction in the number of colonies as higher concentrations of the compound are added. This is a proof of the effectiveness of the compound in treating cancer. The numbers in Table 1 correspond the results shown in FIG. 4. For example, the percent inhibition at 10 μM of the compound is 20% and at 20 μM of the compound is 41%.

Figure 5:
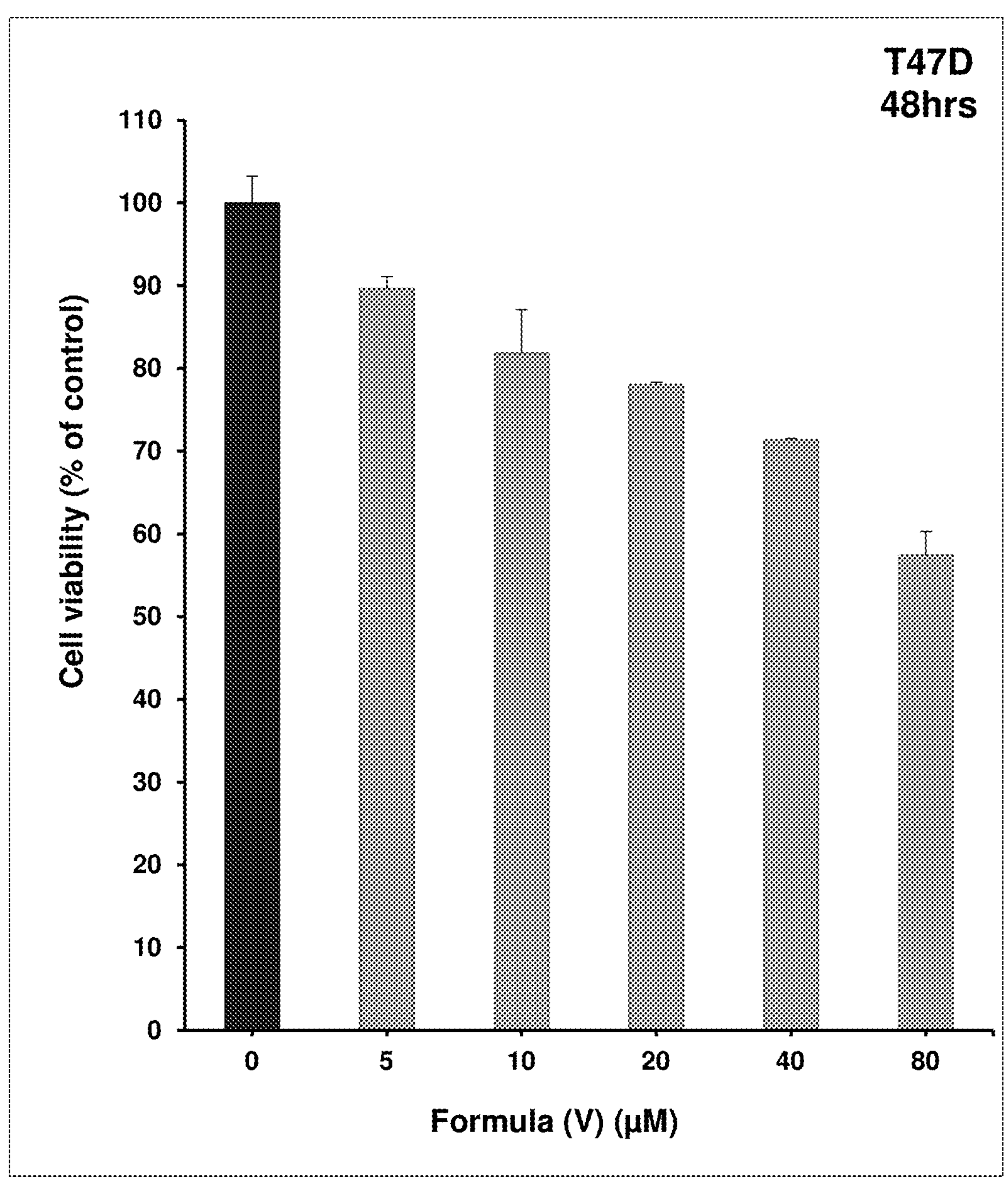
FIG. 5 depicts the cell viability assay on the T47D breast cancer cell line for the compound of Formula (V).

FIG. 5 depicts the cell viability assay on the T47D breast cancer cell line for the compound of Formula (V). The graph shows the cell viability test on the T47D breast cancer cell line after a 48 h treatment with different concentrations of the compound of Formula (V). This graph shows the cell viabilities as percentage of the control. 100% is equivalent to $2568.87 \times 10^4$ luciferase units. The results, at different concentrations, are compared with respect to the untreated control (at 0 μM). It is found that a concentration of 80 μM reduces the cell viability to 57±4% (i.e. $1475.46 \times 10^4$ luciferase units; the standard deviations are from repeated reads done per experiment), meaning that the $IC_{50}$ will be greater than 80 μM.

Figure 6:
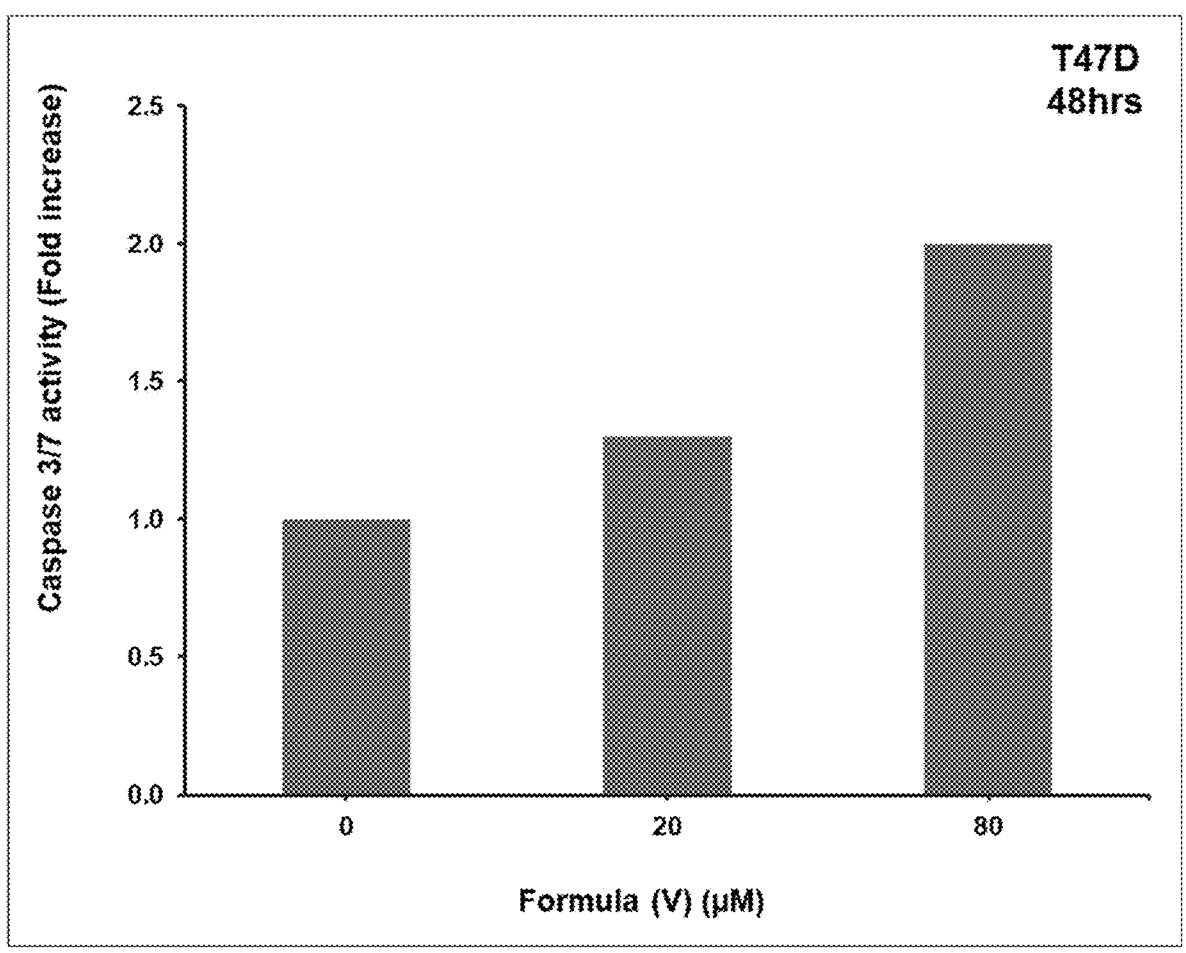
FIG. 6 depicts the caspase 3/7 activity on the T47D breast cancer cell line for the compound of Formula (V).

FIG. 6 depicts the caspase 3/7 activity on the T47D breast cancer cell line for the compound of Formula (V). The caspase 3/7 activity is measured and reported as a "fold increase". In other words, the graph shows the relative change in the caspase 3/7 activity level compared to the baseline control condition. FIG. 6 demonstrates the fold increase in caspase 3/7 activity after 48 hours treatment of the T47D cell line with the compound at two different concentrations relative to the drug-free control baseline (at 0 μM). At a concentration of 20 μM, the caspase 3/7 activity shows a 1.3-fold increase compared to the baseline. It is only at a concentration of 80 μM of the compound that the fold increase reaches 2.0. As caspase 3/7 activation is a hallmark of apoptosis, this indicates that the reduction in cell viability induced by the compound is primarily due to the apoptotic cell death of the T47D cells.

Table 2 below presents the average number of colonies in the T47D cell line from duplicates. It includes results of the untreated control and the treatments with the compound of Formula (V) at concentrations of 0 μM (i.e. control), 20 μM and 80 μM. Additionally, the table shows the reduction in colony number compared to the untreated control-colony.

TABLE 2 average number of colonies in the T47D cell line with the compound of Formula (V) at concentrations of 0 μM (i.e. control), 20 μM and 80 μM.

| (μM) | Number of Colonies | % of inhibition |
|---|---|---|
| 0 | 107 | 0 |
| 20 | 79 | 26 |
| 80 | 58 | 46 |

Figure 7:
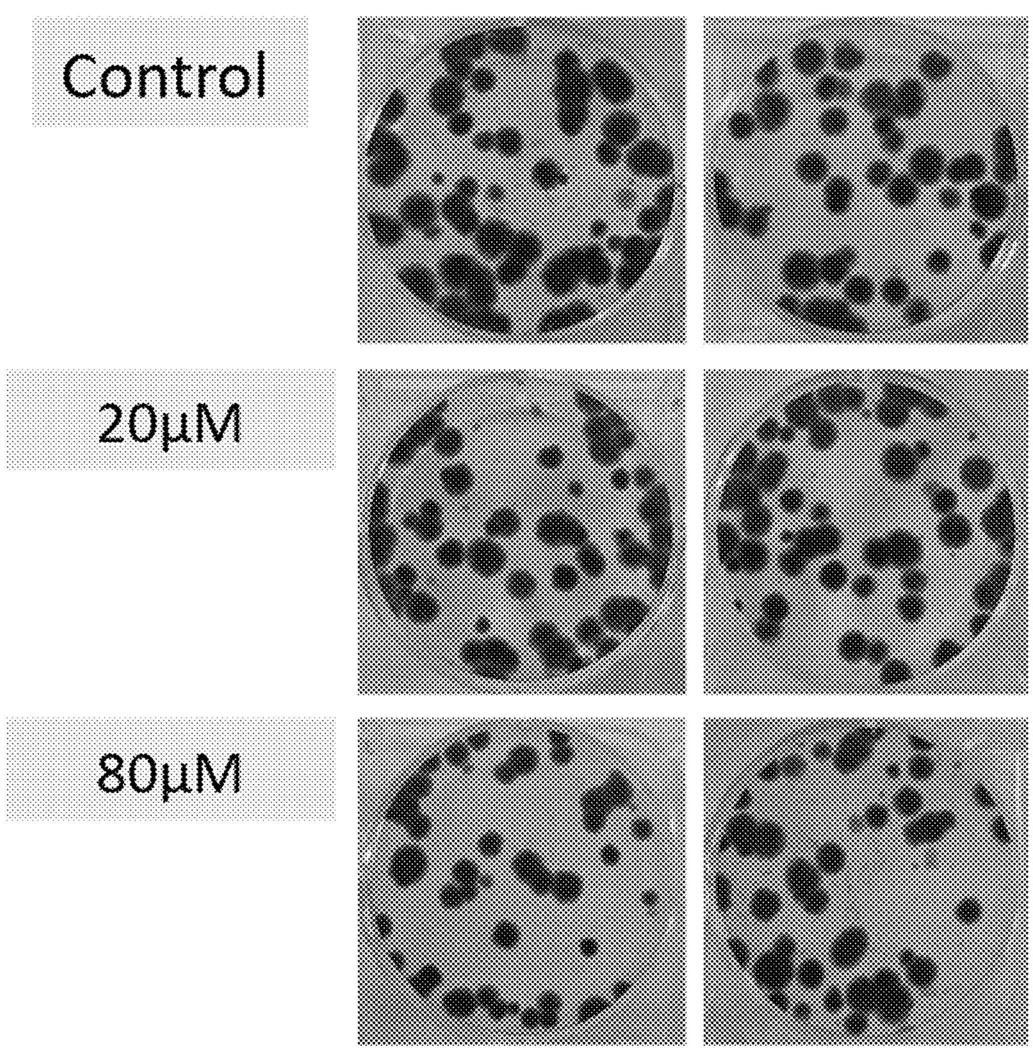
FIG. 7 sets out images showing the T47D colonies at various micro-molar concentrations of the compound of Formula (V).

FIG. 7 sets out images showing the T47D colonies at various micro-molar concentrations of the compound of Formula (V). The images show the T47D colonies, in duplicates (one to the left and one to the right), at 0 μM (i.e. control), 20 μM, and 80 μM of the compound. These images show the reduction in the number of colonies as higher concentrations of the compound are added. This is a proof of the effectiveness of the compound in treating cancer.

An in ovo tumour growth assay is described herein. The in ovo assay surpasses in vitro models by incorporating a living, vascularized system, making it closer to in vivo conditions. Fertilized Leghorn eggs were incubated at 37.5° C. On day 3, egg albumin was aspirated. A small opening was then cut above the CAM and, sealed with a semipermeable adhesive film and kept the incubator until day 9. On day 9, cancer cells, MDA-MB-231, were trypsinized, counted, and centrifuged.

On days 11, 13, and 15, the tumors were treated with 200 μM of the compound of Formula (V). On day 17, the tumors with the rings were extracted from the upper CAM tissue, washed, and weighed. The mean tumor weight of each group was reported. The toxicity effect of the compound of Formula (V) was evaluated at the end of the experiment by comparing the mean alive embryos of each group. Chick embryos' viability was tested by assessing the voluntary movements of the embryos and the pulsation and integrity of the blood vessels. This assay was performed following the approved protocol by the animal ethics committee at the United Arab Emirates University.

Figure 8:
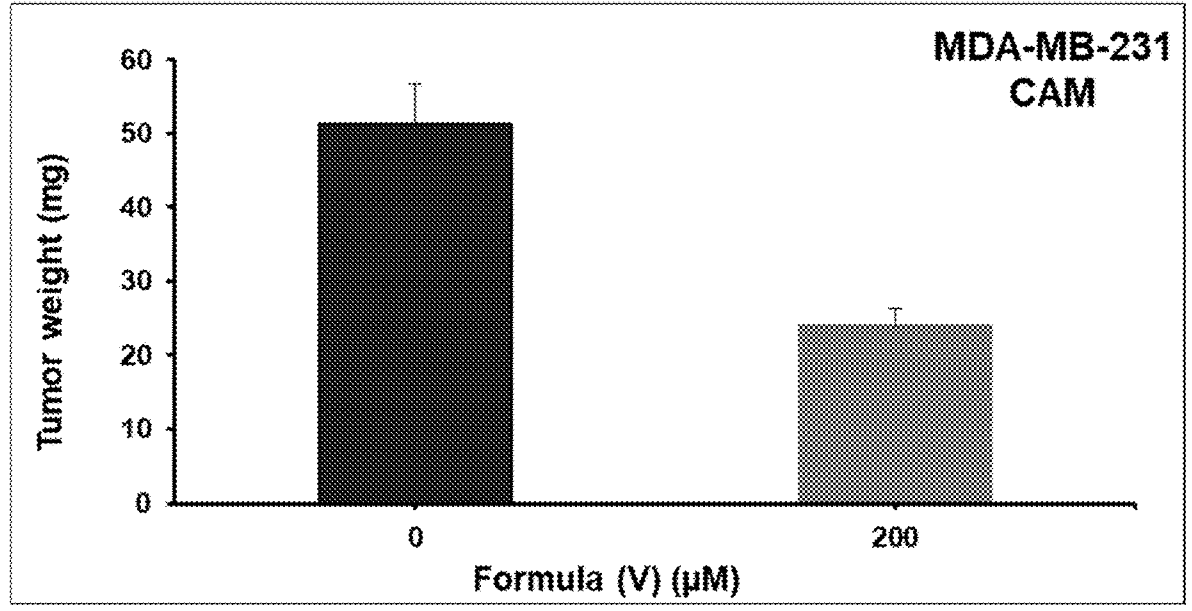
FIG. 8 depicts the average tumor weight±SEM for the 15 eggs per group, measured in the absence of treatment (Control+DMSO) and in the presence of treatment (200 μM of the compound of Formula (V)).

FIG. 8 depicts the average tumor weight±SEM for the 15 eggs per group, measured in the absence of treatment (Control+DMSO) and in the presence of treatment (200 μM of the compound of Formula (V)).

Example 2

In addition to the toxicity measured in the CAM test, additional toxicity evaluations were completed. Information regarding toxicity profiles is set out in Table 3 below.

TABLE 3

| Information on toxicity | |
|---|---|
| LD50 | Toxic doses are often given as LD50 values in mg/kg body weight. The LD50 is the median lethal dose meaning the dose at which 50% of test subjects die upon exposure to a compound. LD50 value generally indicates that a substance has low acute toxicity, which is considered a positive result in toxicity testing. |
| Class: | Toxicity classes are defined according to the globally harmonized system of classification of labelling of chemicals (GHS). LD50 values are given in [mg/kg]:<br>Class I: fatal if swallowed (LD50 ≤ 5)<br>Class II: fatal if swallowed (5 < LD50 ≤ 50)<br>Class III: toxic if swallowed (50 < LD50 ≤ 300)<br>Class IV: harmful if swallowed (300 < LD50 ≤ 2000)<br>Class V: may be harmful if swallowed (2000 < LD50 ≤ 5000)<br>Class VI: non-toxic (LD50 > 5000) |
| Citation from website | Banerjee P., Kemmler E., Dunkel M., Preissner R.: ProTox 3.0: a webserver for the prediction of toxicity of chemicals<br>Nucleic Acids Res (Web server issue 2024); NAR<br>Banerjee P., Eckert O. A., Schrey A. K., Preissner R.: ProTox-II: a webserver for the prediction of toxicity of chemicals.<br>Nucleic Acids Res (Web server issue 2018); NAR |

Table 4 below sets out the toxicity profile of the compound of Formula (V) compared to some examples of FDA-approved breast cancer drugs.

TABLE 4

| Toxicity profiles | | | | |
|---|---|---|---|---|
| | compound of Formula (V) | Cyclophosphamide | Methotrexate Sodium | Thiotepa |
| Class | 3 | 3 | 1 | 1 |
| $LD_{50}$ (mg/kg body weight) | 200 | 94 | 3 | 2 |

It is apparent from Table 4 that the compound of Formula (V) has a safer profile than all the drugs listed in this table. The compound of Formula (V) is in class 3, while the FDA-approved breast cancer drugs (methotrexate sodium and thiotepa) are in class 1 meaning they are fatal if swallowed, and are therefore, much more toxic. The FDA-approved breast cancer drug, cyclophosphamide, is in the same class (class 3) as the compound of Formula (V), however it has a smaller LD50 of 94 mg/kg body weight, meaning that it is comparably lethal at much lower concentrations.

What is claimed is:

1. A method of treating breast cancer in a subject in need thereof, comprising: administering to the subject:

(i) a therapeutically effective amount of a compound of Formula (II):

(II)

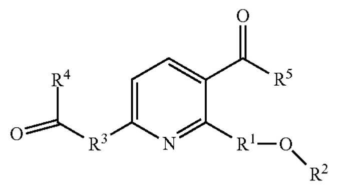

wherein:

$R^1$ is optionally substituted phenyl;

$R^2$ is optionally substituted phenyl;

$R^3$ is independently selected from the group consisting of optionally substituted heterocyclyl or —$C_{1-8}$ alkyl-heterocyclyl, wherein the heterocyclyl and —$C_{1-8}$ alkyl-heterocyclyl are each 3- to 7-membered comprising 1 or 2 heteroatoms selected from nitrogen and oxygen;

$R^4$ is independently selected from the group consisting of optionally substituted $C_{1-8}$ alkyl —$C_{2-8}$ alkenyl or —$C_{2-8}$ alkynyl; and $R^5$ is independently selected from the group consisting of —$N(R)_2$, wherein R is selected from the group comprising a hydrogen and/or an alkyl; N(HR), wherein R is selected from the group comprising a hydrogen, an alkyl or optionally substituted $C_{1-8}$ alkyl; or (ii) a pharmaceutically acceptable salt, co-crystal, polymorph hydrate, solvate, prodrug, bioisostere, or a stereoisomer thereof.

2. The method according to claim 1, wherein $R^1$ and $R^2$ are phenyl.

3. The method according to claim 1, wherein the method comprises administering to the subject a therapeutically effective amount of a composition comprising a therapeutically effective amount of the compound of Formula (II), or a pharmaceutically acceptable salt, co-crystal, polymorph, hydrate, solvate, prodrug, or a stereoisomer thereof, and one or more pharmaceutical excipients and/or carriers.

4. The method according to claim 1, wherein the method comprises administering to the subject:

(i) a therapeutically effective amount of a compound of Formula (III):

(III)

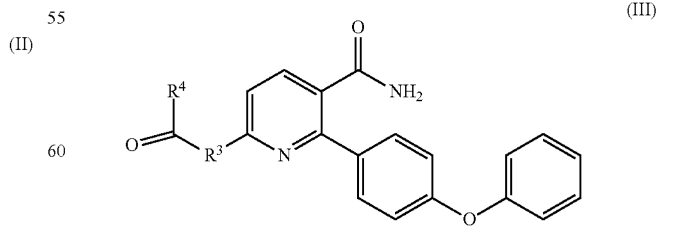

wherein $R^3$ is independently selected from the group consisting of optionally substituted heterocyclyl or —$C_{1-8}$ alkyl-heterocyclyl, wherein the heterocyclyl and $—C_{1-8}$ alkyl-heterocyclyl are each 3- to 7-membered comprising 1 or 2 heteroatoms selected from nitrogen and oxygen;

$R^4$ is independently selected from the group consisting of optionally substituted $C_{1-8}$ alkyl, $—C_{2-8}$ alkenyl or $—C_{2-8}$ alkynyl; or (ii) a pharmaceutically acceptable salt, co-crystal, polymorph, hydrate, solvate, prodrug, bioisostere, or a stereoisomer thereof.

5. The method according to claim 4, wherein:

$R^3$ is optionally substituted heterocyclyl, wherein the heterocyclyl is 3- to 7-membered comprising 1 or 2 heteroatoms selected from nitrogen and oxygen; and $R^4$ is independently selected from the group consisting of optionally substituted $C_{1-8}$ alkyl, $—C_{2-8}$ alkenyl, or $—C_{2-8}$ alkynyl.

6. The method according to claim 4, wherein the method comprises administering to the subject a therapeutically effective amount of a composition comprising a therapeutically effective amount of the compound of Formula (III), or a pharmaceutically acceptable salt, co-crystal, polymorph, hydrate, solvate, prodrug, or a stereoisomer thereof, and one or more pharmaceutical excipients and/or carriers.

7. The method according to claim 1, wherein the method comprises administering to the subject:

(i) a therapeutically effective amount of a compound of Formula (IV):

(IV)

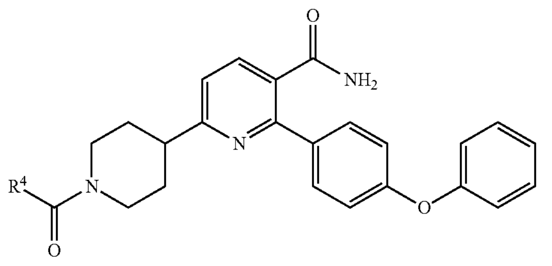

wherein $R^4$ is independently selected from the group consisting of optionally substituted $C_{1-8}$ alkyl, $—C_{2-8}$ alkenyl and $—C_{2-8}$ alkynyl; or (ii) a pharmaceutically acceptable salt, co-crystal, polymorph, hydrate, solvate, prodrug, bioisostere, or a stereoisomer thereof.

8. The method according to claim 7, wherein $R^4$ is independently selected from the group consisting of optionally substituted $—C_{2-8}$ alkenyl or $—C_{2-8}$ alkynyl.

9. The method according to claim 7, wherein the method comprises administering to the subject a therapeutically effective amount of a composition comprising a therapeutically effective amount of the compound of Formula (IV), or a pharmaceutically acceptable salt, co-crystal, polymorph, hydrate, solvate, prodrug, or a stereoisomer thereof, and one or more pharmaceutical excipients and/or carriers.

10. A method of treating breast cancer in a subject in need thereof, comprising:

administering to the subject:

(i) a therapeutically effective amount of a compound of Formula (V):

(V)

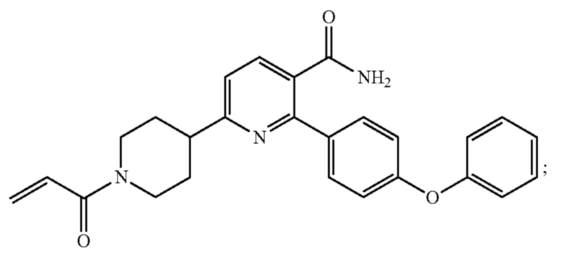

;

or (ii) a pharmaceutically acceptable salt, co-crystal, polymorph, hydrate, solvate, prodrug, bioisostere, or a stereoisomer thereof.

11. The method according to claim 10, wherein the method comprises administering to the subject a therapeutically effective amount of a composition comprising a therapeutically effective amount of the compound of Formula (V), or a pharmaceutically acceptable salt, co-crystal, polymorph, hydrate, solvate, prodrug, or a stereoisomer thereof, and one or more pharmaceutical excipients and/or carriers.

12. The method of claim 11, wherein the treatment kills at least 50% of breast cancer cells.

13. The method of claim 1, wherein the subject is a mammal.

14. The method of claim 13, wherein the mammal is a human.

15. The method of claim 1, comprising administering one or more additional therapeutic agents, wherein the additional therapeutic agents are administered prior to, concurrently with, or subsequently to the administration of the compound of Formula (II) or a composition comprising the compound of Formula (II).

16. The method of claim 10, comprising administering one or more additional therapeutic agents, wherein the additional therapeutic agents are administered prior to, concurrently with, or subsequently to the administration of the compound of Formula (V) or a composition comprising the compound of Formula (V).

* * * * *